(12) United States Patent
Weersink et al.

(10) Patent No.: US 9,138,597 B2
(45) Date of Patent: Sep. 22, 2015

(54) QUANTITATIVE ENDOSCOPY

(75) Inventors: Robert Weersink, Toronto (CA); Andrew Hope, Toronto (CA); Jeff Siewerdsen, Baltimore, MD (US); David Jaffray, Etobicoke (CA); Aidin Kashigar, London (CA); Michael Daly, Toronto (CA); Jonathon Eubank, Cambrige (CA); John Cho, Etobicoke (CA)

(73) Assignee: University Health Network, Toronto (CA)

( * ) Notice: Subject to any disclaimer, the term of this patent is extended or adjusted under 35 U.S.C. 154(b) by 749 days.

(21) Appl. No.: 13/320,375

(22) PCT Filed: May 13, 2010

(86) PCT No.: PCT/CA2010/000749
§ 371 (c)(1),
(2), (4) Date: Feb. 29, 2012

(87) PCT Pub. No.: WO2010/130056
PCT Pub. Date: Nov. 18, 2010

(65) Prior Publication Data
US 2012/0155731 A1    Jun. 21, 2012

Related U.S. Application Data

(60) Provisional application No. 61/178,319, filed on May 14, 2009.

(51) Int. Cl.
*G06K 9/00* (2006.01)
*A61N 5/10* (2006.01)
(Continued)

(52) U.S. Cl.
CPC ............. *A61N 5/103* (2013.01); *G06T 7/0032* (2013.01); *A61N 5/1039* (2013.01); *G06F 19/321* (2013.01); *G06T 2207/10068* (2013.01); *G06T 2207/30004* (2013.01)

(58) Field of Classification Search
USPC .......... 382/100, 128–132; 600/101, 109, 112, 600/114, 117, 118, 139, 145, 173, 420, 424, 600/427, 437, 415, 416, 562, 587; 606/1, 606/45, 130; 700/57, 245; 703/2, 6, 11; 345/420, 427, 424, 629, 630
See application file for complete search history.

(56) References Cited

U.S. PATENT DOCUMENTS 6,246,898 B1    6/2001  Vesely et al.
6,346,940 B1 *  2/2002  Fukunaga ..................... 345/427
(Continued)

FOREIGN PATENT DOCUMENTS

WO    2006/109219    10/2006
WO    2008/095068 A1    8/2008
WO    2008/111070 A2    9/2008

OTHER PUBLICATIONS

International Search Report issued in PCT/CA2010/000721 on Aug. 16, 2010 (3 pp.).
(Continued)

*Primary Examiner* — Hadi Akhavannik
(74) *Attorney, Agent, or Firm* — Nixon Peabody LLP; David S. Resnick; Leena H. Karttunen Contarino

(57) ABSTRACT

A method, computer program product and processor for quantitatively registering a 2D endoscopic ROI in a 3D volumetric imaging dataset. An endoscopic dataset and a volumetric imaging are registered to a common coordinate system. A 2D endoscopic ROI is generated within the endoscopic imaging dataset. A 3D surface ROI is generated within the volumetric imaging dataset corresponding to the 2D endoscopic ROI, based on a projection of the 2D endoscopic ROI to the registered common coordinate system.

11 Claims, 9 Drawing Sheets

(51) Int. Cl.
*G06T 7/00* (2006.01)
*G06F 19/00* (2011.01)

(56) References Cited

U.S. PATENT DOCUMENTS

| | | | |
|---|---|---|---|
| 2003/0000535 | A1 | 1/2003 | Galloway, Jr. et al. |
| 2005/0033142 | A1 | 2/2005 | Madden et al. |
| 2005/0033149 | A1 | 2/2005 | Strommer et al. |
| 2005/0272971 | A1* | 12/2005 | Ohnishi et al. ............ 600/101 |
| 2006/0234994 | A1 | 10/2006 | Rasche et al. |
| 2007/0055128 | A1 | 3/2007 | Glossop |
| 2007/0135803 | A1 | 6/2007 | Belson |
| 2008/0137924 | A1* | 6/2008 | Boese et al. ............... 382/128 |
| 2008/0207997 | A1* | 8/2008 | Higgins et al. ............ 600/114 |
| 2008/0230705 | A1 | 9/2008 | Rousso et al. |
| 2009/0281452 | A1 | 11/2009 | Pfister et al. |
| 2010/0041949 | A1* | 2/2010 | Tolkowsky ................ 600/109 |

OTHER PUBLICATIONS

Rosenthal, et al, "Importance of patient examination to clinical quality assurance in head and neck radiation oncology", Head and Neck-Journal for the Sciences and Specialties of the Head and Neck, 28: 967, 2006.

Sharma, et al, "The utility of a novel narrow band imaging endoscopy system in patients with Barrett's esophagus", Gastrointestinal Endoscopy, 64: 167, 2006.

Wilson, B. C., "Detection and treatment of dysplasia in Barrett's esophagus: a pivotal challenge in translating biophotonics from bench to bedside", Journal of Biomedical Optics, 12, 2007.

Kara, et al, "Endoscopic video-autofluorescence imaging followed by narrow band imaging for detecting early neoplasia in Barrett's esophagus", Gastrointestinal Endoscopy, 64: 176, 2006.

Fried, et al, "Image-Guidance for Endoscopic Sinus Surgery", Laryngoscope, 118: 1287, 2008.

Caversaccio, et al, "Augmented reality endoscopic system (ARES): preliminary results" Rhinology, 46: 156, 2008.

Higgins, et al, "3D CT-Video Fusion for Image-Guided Bronchoscopy", Computerized Medical Imaging and Graphics, 32: 159, 2008.

Lapeer, R., Chen, M. S., Gonzalez, G. et al.: Image-enhanced surgical navigation for endoscopic sinus surgery: evaluating calibration, registration and tracking. International Journal of Medical Robotics and Computer Assisted Surgery, 4: 32, 2008.

Lindbergh, et al, "Reduced scattering coefficient determination by non-contact oblique angle illumination: methodological considerations—art. No. 643501", Optical Interactions with Tissue and Cells XVIII, 6435: 14350, 2007.

Lin, et al, "Measurement of tissue optical properties by the use of oblique-incidence optical fiber reflectometry", Applied Optics, 36: 136, 1997.

Gebhart, et al, "Experimental and simulated angular profiles of fluorescence and diffuse reflectance emission from turbid media", Applied Optics, 44: 4884, 2005.

Qu, et al, "Correction of geometrical effects on fluorescence imaging of tissue", Optics Communications, 176: 319, 2000.

Qu, et al, "Excitation-and-collection geometry insensitive fluorescence imaging of tissue-simulating turbid media", Applied Optics, 39: 3344, 2000.

Wang, et al, "Anatomical reconstruction from endoscopic images: Toward quantitative endoscopy" American Journal of Rhinology, 22: 47, 2008.

\* cited by examiner

Real 2D View $(u,v)_S$

Virtual 2D View $(u,v)_{CT}$

Mesh
$(u,v)_{CT}$

QUANTITATIVE ENDOSCOPY

CROSS-REFERENCE TO RELATED APPLICATIONS

This application is a 35 U.S.C. §371 National Phase Entry Application of International Application No. PCT/CA2010/000749, filed May 13, 2010, which designates the United States, and which claims benefit under 35 U.S.C. §119(e) of the U.S. provisional application No. 61/178,319, filed on May 14, 2009, the contents of which are herein incorporated by reference in their entirety.

TECHNICAL FIELD

The present disclosure relates generally to endoscopy, in particular methods for quantitative endoscopy suitable for treatment planning in radiotherapy.

BACKGROUND

Target delineation in many cancers is required when employing intensity modulated radiation therapy (IMRT). Methods to identify targets for delineation typically rely on volumetric imaging (e.g., computational tomography (CT), magnetic resonance (MR), positron emission topography (PET)) combined with non-volumetric imaging such as physical exam findings and endoscopy. At times, endoscopy and physical exams reveal areas of visible or palpable tumour extension which are not clearly demonstrated on volumetric imaging. However, interpreting endoscopy images as it relates to the volumetric imaging may be subject to error. This may be at least partly because localizing disease usually relies on remembering the relationship of the disease to fixed anatomic landmarks that are visible on both the volumetric imaging and endoscopy, which, by its nature, may be imprecise or inaccurate.

Radiotherapy planning is becoming more and more conformal, leading to concern that a tumor may be unintentionally 'missed' during the planning process and a desire to accurately delineate tumors during the planning process. One method of addressing this is to use relatively large planning margins to minimize the risk of missing tumors. However, using large margins to minimize this risk is associated with increased risk of morbidity and late side-effects. Ideally, one would like to limit the treatment to the tumor and avoid normal tissue as much as possible. Recent research has suggested that high quality radiation therapy (including proper identification of target) can be associated with a survival advantage. Of course, identifying the target is a useful important step in treatment of any malignancy[1].

In patients with endoluminal malignancies, including, for example, head and neck, esophagus, bronchial, lung and lower gastrointestinal cancers, it is well accepted that the physical examination plays a critical role in determination of the 'target' for radiation therapy. Often, physical exam findings can reveal areas of visible or palpable tumor extension which are not clearly demonstrated on volumetric imaging studies. Using indirect fiberoptic endoscopy visualization of the nasopharynx, oropharynx, and larynx, for example in head and neck cancers, can reveal subtle changes which alter the target that will be planned for radiation treatment. Variations on standard white light endoscopy can also be used to improve target delineation. Narrow band imaging[2] and autofluorescence[3] endoscopies have demonstrated increased sensitivity in determining the extent of disease, although at a cost in specificity. The combination of all of these has been shown to improve, for example, the early diagnosis of esophogeal disease such as Barrett's esophagous, and would possibly improve diagnosis in head and neck cancer as well[4]. This combination has also been found to be useful in other cancers, including, for example, lung and colon cancers. At present, the visual information available during endoscopy cannot be directly (or quantitatively) used in the planning process, rather, the clinician 'interprets' (i.e., qualitatively evaluates) the physical exam findings relative to the available volumetric planning data to create a 'composite' target. This usually requires reliance on relationships to anatomic landmarks or structures which are visible on CT and endoscopy.

SUMMARY

The present disclosure may provide technology for guiding an endoscope in volumetric imaging space, such as CT imaging, during a surgical procedure. This may be useful in providing a practitioner with information on where the viewers are located within the imaged volume. Often, volumetric imaging may be used to diagnose and identify the location of disease, and the removal or therapy for the disease may be performed using endoscopy as a visualization tool. In accordance with the present disclosure, the diagnosis may be performed using endoscopy while treatment may be performed using volumetric imaging. The quantitative registration of the two data sets (endoscopic imaging and volumetric imaging) may enable the transfer of disease identified in the endoscopy image to the volumetric imaging space.

In particular, this technology may be useful for contouring disease visible in the endoscopic image and registering the contoured region of interest with a volumetric imaging dataset. Any suitable volumetric imaging dataset may be used, including, for example, computer tomography (CT), magnetic resonance (MR) or positron emission tomography (PET) imaging datasets. Any suitable endoscopic datasets may be used, including, for example, white light, fluorescence (both endogenous and using contrast agents), ultrasound, narrow-band imaging, or surgical endoscopic datasets may be used.

In some aspects, the present disclosure provides a method for quantitatively registering a 2D endoscopic region of interest (ROI) in a 3D volumetric imaging dataset, the method comprising: receiving signals representing the volumetric imaging dataset; receiving signals representing an endoscopic dataset from an endoscope, the endoscopic dataset including an endoscopic imaging dataset and a tracking dataset, the tracking dataset including information about the position and orientation of the endoscope; wherein coordinates of the endoscopic dataset and coordinates of the volumetric imaging dataset are registered to a common coordinate system; receiving a definition of the 2D endoscopic ROI within the endoscopic imaging dataset; generating a 3D surface ROI within the volumetric imaging dataset corresponding to the 2D endoscopic ROI, based on a projection of the 2D endoscopic ROI to the registered common coordinate system; and transmitting signals representing the generated 3D surface ROI.

In some aspects, the method described above may be used for treatment planning in radiotherapy.

In some aspects the present disclosure also provides, a computer program product, a processor, and a treatment planning system for carrying out the method described above.

BRIEF DESCRIPTION OF THE DRAWINGS

Reference will now be made to the drawings, which show by way of example embodiments of the present disclosure, and in which.

DETAILED DESCRIPTION

Figure 1:
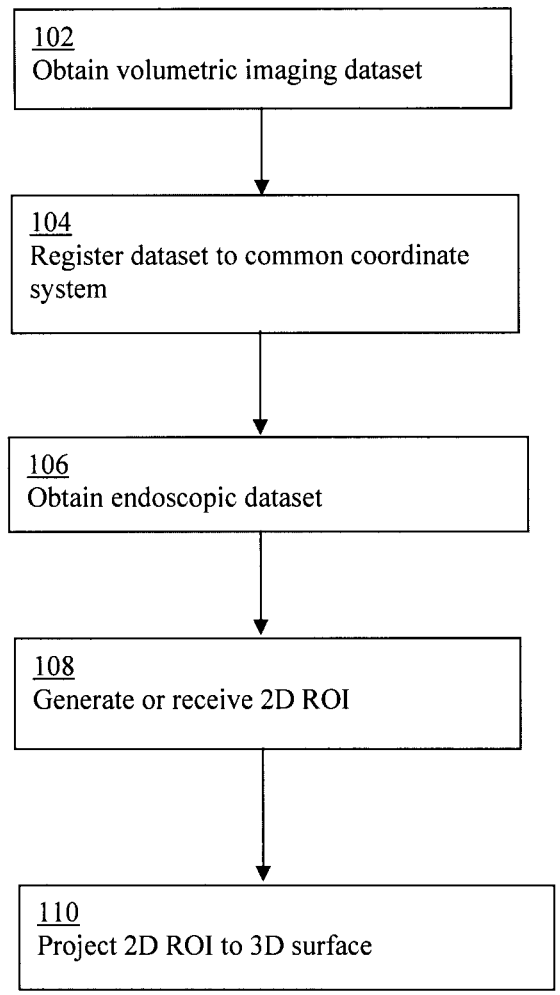
FIG. 1 illustrates an example of a method of quantitatively registering a 2D endoscopic ROI with 3D volumetric imaging data in accordance with some aspects of the present disclosure.

A method to accurately overlay endoscopic images onto a surface within a volumetric imaging dataset (such as a treatment planning CT) may help to simplify and potentially improve the process of tumor delineation.

Example methods of "quantitative endoscopy" technology are described, in which the endoscopic information may be retrospectively and quantitatively registered with volumetric imaging data, such as CT information, during the contouring process. Here the term "quantitative" may be used to refer to the quantitatively determined spatial coordinates of the image with respect to the volumetric frame of reference.[14]

There is a large field of image-guided interventions that has developed. This includes the development of volumetric image registration techniques, deformable (or non-rigid) registration, tracking and navigation of surgical tools and needles and augmented visualization systems. Image guidance may provide the clinician with the ability to visualize the extent of disease in 3 dimensions, which may assist in planning and executing a therapy, assessing progress during a procedure and modifying the procedure based on this information.

Volumetric imaging, such as CT, and endoscopic information provide complimentary clinical data: volumetric imaging may provide high resolution volumetric anatomical information while endoscopy may provide color, texture and/or fine morphological information. For cancers in endoluminal tracts including, for example, head and neck, lung or esophagus, amount others, which typically occur on the epithelial layer or the mucosal layer, both modalities may be used to determine the full extent of disease: endoscopy may identify tumor margins on the tissue surface with greater accuracy than volumetric imaging (e.g., CT), and volumetric imaging may indicate infiltration of tumour. Although the description may refer to CT in particular, any suitable volumetric imaging technology may be used, and CT is only provided as a non-limiting example.

3D to 2D registration is often employed in surgical interventions or in image-guided insertions. In surgery, the 2D image dataset may be a surgical microscope or endoscope. Calibrating the position and orientation of these systems with a 3D image dataset may enable an overlay of real 2D images from the microscope or endoscope with virtual 2D images based on a rendering of the 3D image dataset from the same perspective as the endoscope or microscope camera. Thus, a projection of 3D structures onto a 2D plane is provided to the clinician during the procedure, which may be augmented with color and texture information from the real 2D image. While the treatment plan may have been conceived in a 3D coordinate system, the actual delivery is in real world coordinates based on the clinician's 2D visual field.

Co-registration of 2D and 3D image information has been employed in surgical procedures;[5, 6]. Research in this field has primarily focused on bronchoscope tracking for guiding biopsy[7], or in guiding surgical procedures in the head and neck[5, 8]. In these cases, the treatment path uses CT to target the disease and plan the therapy with targeted tissue identified and contoured using the volumetric data set. This information is used to develop the treatment plan, including, for example, surgical excision, and biopsy targeting. During the procedure, endoscopy is used to essentially "extend" the clinicians eye into the luminal volume. The goal in most research in this field is to track the position and orientation of the endoscope with the purpose of identifying site lines during the procedure relative to the CT frame of reference, which is being used to guide the procedure. In these cases, endoscopy may provide further diagnostic information, but the information is typically only required in real time. Further, the 2D image is typically fixed to the imaged 2D plane (i.e., located in the plane of the endoscopic camera), and the plane is merely positioned and aligned in the 3D CT frame of reference to match the viewing plane of the endoscopic camera. Specific features in the 2D image cannot be located in their actual 3D position within the CT frame of reference.

For radiation treatment planning in sites with hollow structures sites, such as the head and neck, esophagus, etc., the treatment path may be reversed. Since many of the cancers are located superficially on the epithelial layers or the mucosal layer, diagnostic information on tumour extent may be primarily derived from endoscopy. However, the treatment planning and delivery of radiation may be based on contouring and planning in the volumetric (e.g., CT) frame of reference. Conventionally, information acquired during the endoscopy procedure is transferred to the volumetric frame of reference by the clinician visually (i.e., qualitatively) identifying common anatomical landmarks in both data sets, a process fraught with potential inaccuracies, since it is dependent on the skill of the clinician. It would be useful to have a process to more accurately register the 2D endoscopic images that possess clinical information to the 3D volumetric dataset in which contouring occurs. It would also be useful to have a process within this contouring procedure to assess if the contoured ROIs cover the extent of disease identified during endoscopy.

The present disclosure describes technology that may register endoscopic images to volumetric images (e.g., CT images) by tracking and registering the position and orientation of the endoscope to the volumetric image set. This information may then be used in software which may overlay both data sets in the treatment planning space. The planner may identify regions of disease in the endoscopy image, and since the endoscopy image and volumetric datasets have been co-registered, these same regions may therefore be identified in the volumetric dataset. The regions thus contoured may be stored for use in treatment planning software, for example using standard DICOM® structure format.

The present disclosure describes methods for contouring of tissues (e.g., tumor tissues or tissues/organs at risk) identified in 2D endoscopic images and quantitative registration of these contoured regions with 3D volumetric imaging datasets (e.g., CT datasets). An example embodiment of the method employs endoscopic tracking technology, which provides relatively accurate spatio-temporal registration of the endoscope position and orientation with volumetric datasets. The endoscopic information may be retrospectively and quantitatively registered with volumetric information, for example during the contouring process.

The disclosed methods may involve one or more of: i) simultaneous storage of the endoscopic, volumetric imaging, and tracking information, methods of fusing (i.e., registering) and visualizing the data to aid in contouring, and iii) methods of converting 2D x,y data into a 3D coordinate system. The registration of 2D endoscopic imaging data with 3D volumetric imaging data may help to improve the definition of gross tumor volumes (GTV), for example in head and neck and esophageal cancers, by helping to ensure the inclusion of all or substantially all visible disease observed during clinical examination and by helping to decrease contouring variability. Such an approach may be useful in the field of radiation treatment planning and in the field of 2D/3D tracking and registration.

Unlike conventional registration methods, the methods and techniques of the present disclosure may provide for registration of 2D information to a 3D treatment planning and delivery system, such as for radiotherapy. Rather than providing 2D information to augment a 2D view rendered from a 3D image, as in conventional methods, the presently disclosed technology may allow for a contour or region of interest to be defined in 2D, and projecting this 2D ROI to a 3D topography. This projected 3D topography may be displayed in the 3D image, such that information and features from the 2D information is located and displayed within a 3D space. The projected 3D topography may also be used for treatment planning for radiotherapy, for example by allowing for detection of epithelial or surface tumors within the 3D treatment planning space. The projected 3D topography may also be useful in other procedures, for example endosurgery or other surgical procedures. The disclosed methods and techniques may be a counter-intuitive inversion of the typical treatment scheme from 3D planning to 2D delivery.

The disclosed methods and techniques may be useful for radiotherapy treatment planning and delivery because the CT image dataset typically used for treatment planning and delivery does not contain all of the necessary diagnostic information required to define the treatment target, in particular in the case of cancers in the head and neck, lung, esophagus or any other sites which originate as superficial lesions. The extent of disease progression along the surface of these organs is not always evident in CT imaging. 2D endoscopic imaging provides information not available in the 3D CT image, however for the purpose of treatment planning and delivery, it is desirable to locate the 2D endoscopic information within the 3D CT treatment planning space.

An example method for registration of endoscopic ROIs is now described with reference to FIG. 1.

At 102, a 3D volumetric dataset (e.g., a standard CT simulation image) is obtained. The volumetric dataset may be used as the baseline dataset for the remainder of the data collection. The volumetric dataset may include one or more markers (e.g., imaged external fiducial markers), which may be used for registration, as described below.

At 104, the volumetric imaging dataset is registered (e.g., in real-time) to a common coordinate system (e.g., the "real world" space), which may be navigated by an endoscope. This may be done by registering the markers of the volumetric dataset. Registration may also be done for the endoscopic dataset. Registration may take into account patient position, tracking of the endoscope and endoscope camera calibration. For example, the endoscope may include a miniature tracking sensor, allowing real-time tracking of the position and orientation of the endoscope through the co-registered navigation and image space.

Typically, registration may transform position and orientation information from the patient (i.e., real world), CT image and endoscopic frames of reference into a common frame of reference or common coordinate system. This may be achieved, for example, by using fiducial markers on the patient that may be identified on the CT image, and "observed" by the tracking system used to track the position of the endoscope. Suitable software that completes this registration task may, for example, be similar to or adapted from software for image guided surgery.

In general, registration of the volumetric imaging dataset and the endoscopic dataset to a common coordinate system (e.g., the "real world" coordinate system) may be based on markers (e.g., fiducial markers) and/or features (e.g., image features or anatomical features). Although the datasets have been described as being registered to a common real world coordinate system, the volumetric and endoscopic datasets may also be registered to each other only, or to another coordinate system. Suitable registration systems for tracking fiducial markers may include, for example, optical tracking systems (e.g., using stereoscopic cameras, with passive or active markers) or electromagnetic tracking systems.

At 106, an endoscopic dataset is obtained. The endoscopic dataset may include an endoscopic imaging dataset and a tracking dataset. The endoscopic imaging dataset may include 2D images of tissues of interest (e.g., suspicious lesions or possible tumors) and the tracking dataset may include tracking coordinates (e.g., position coordinates (x, y, z) and orientation coordinates ($\Phi$, $\varphi$, $\theta$)). In some examples, the endoscopic dataset may be obtained prior to registration, such as where the endoscopic dataset and the volumetric dataset are registered to each other.

For example, where the endoscopic dataset is obtained prior to registration of the volumetric imaging dataset, multiple 2D images from the endoscopic dataset may be used with respective known tracking coordinates for each 2D image to calculate a 3D model (e.g., a 3D surface) that can be registered to a 3D structure in the 3D volumetric imaging dataset. This may be useful, for example, where fiducial or anatomical markers are not used for co-registration of the datasets.

The endoscopic dataset may be stored, for example in a database of a processor. The volumetric dataset may be stored in the same or different database. The endoscopic dataset may be associated with the corresponding volumetric dataset, for example by a pointer to the corresponding data stored in the database. Where the endoscopic and volumetric datasets are separately stored, there may be an index file stored to relate the datasets to each other. Where the datasets are separately stored, during the ROI generation and/or projection described below, information from respective datasets may be transmitted or accessed by a common database or processor.

Figure 3:
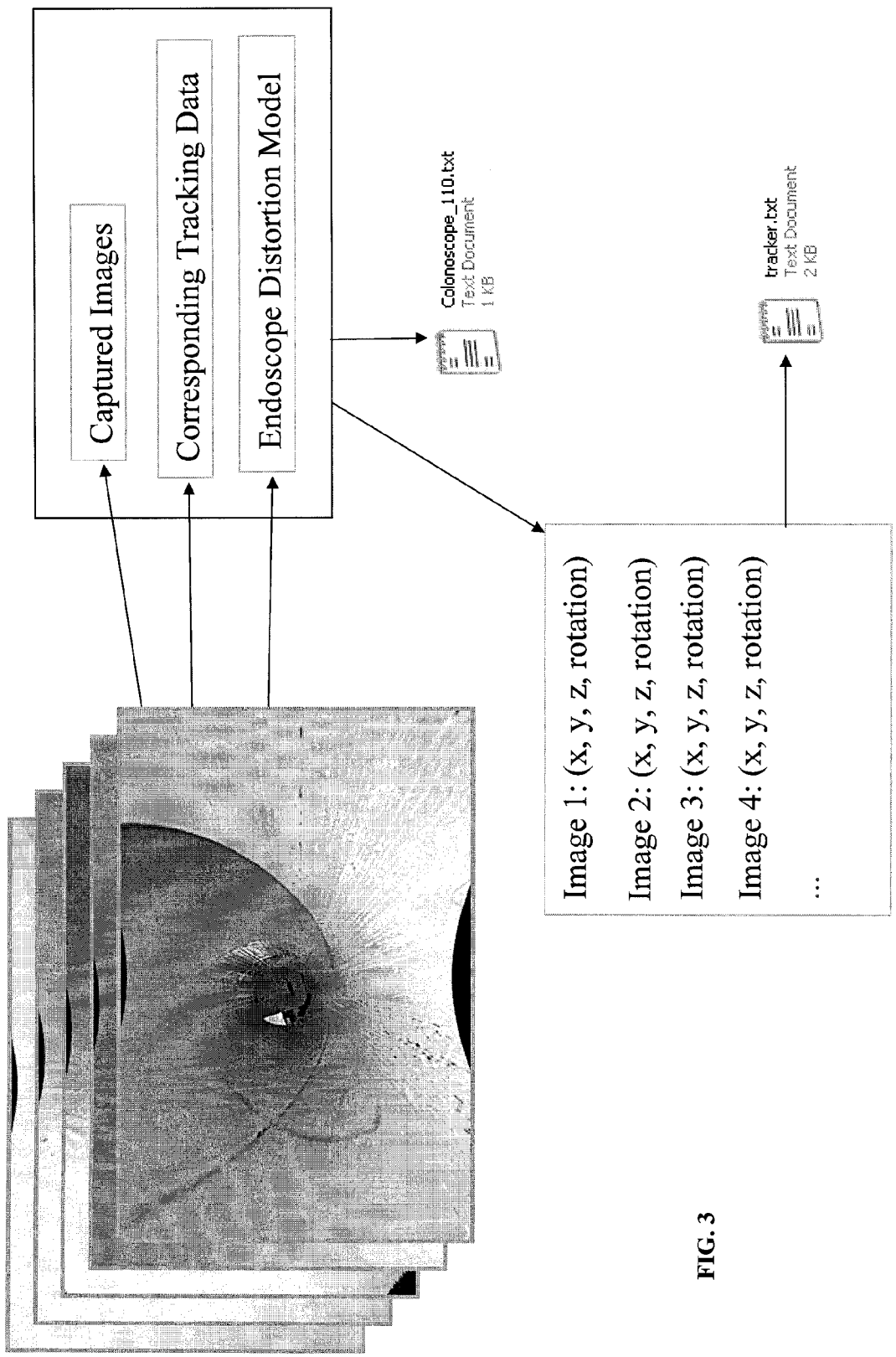
FIG. 3 illustrates an example data flow suitable for the method of FIG. 1.

For example, the endoscopic imaging dataset may be stored with the respective tracking dataset in a single data format. Data collection and storing of the data may be functions provided by the same software that performs registration, or by different software. Data collection and storing of data may use a database that enables images to be recalled based on requests for positions and orientations, for example. With each image file, there may be associated tracking data stored in a separate file, linked to the respective captured image at the tracked location. An example of this is illustrated in FIG. 3, which shows an outline of the data handling. During a single patient screening session, the endoscopic still images or video may be captured and stored in a database. Simultaneously, the tracking coordinates may be stored in a tracking information file. A camera distortion model may also be stored (e.g., a pre-calculated model, based on camera properties). This information may be used for generating contours or ROIs, described below.

For generating contours or ROIs, the endoscopic dataset and the volumetric dataset may both be accessed. Other parameters, such as camera calibration, may also be stored in the database and accessed for contour generation.

At 108, a 2D contour (e.g., around suspicious lesions or other tissues of interest) is generated in the endoscopic imaging dataset. The 2D contour may be generated based on a manual selection of points in the 2D image by a clinician. The generation of the contour may include generation of a 2D ROI that defines points within the contour, such as a mesh (e.g., a triangular mesh) within the contour, for example to allow for identification of any features within the 2D contour. In some examples, the 2D ROI may be generated ahead of time (e.g., in a previous manual selection) and the pre-defined or pre-selected ROI may simply be received (e.g., as transmitted signals).

At 110, the 2D ROI is projected onto a 3D topography or surface in the volumetric imaging dataset. This may be done, for example, by projecting the mesh for each ROI onto a corresponding 3D surface based on the registration of the markers performed at 104. Thus, a 3D surface ROI (e.g., a 3D mesh) is generated that identifies the position of the 2D ROI, and any features within the 2D ROI, within the 3D volumetric imaging space.

In some examples, the contouring software may be designed to read in both the volumetric dataset and the tracked endoscopic dataset. Where the volumetric dataset and the endoscopic dataset are registered to a common coordinate system, the common coordinate system may be used to co-register the volumetric dataset and the endoscopic dataset. Where the endoscopic dataset and the volumetric dataset are already registered to each other, it may not be necessary to co-register the datasets to each other again.

Figure 4:
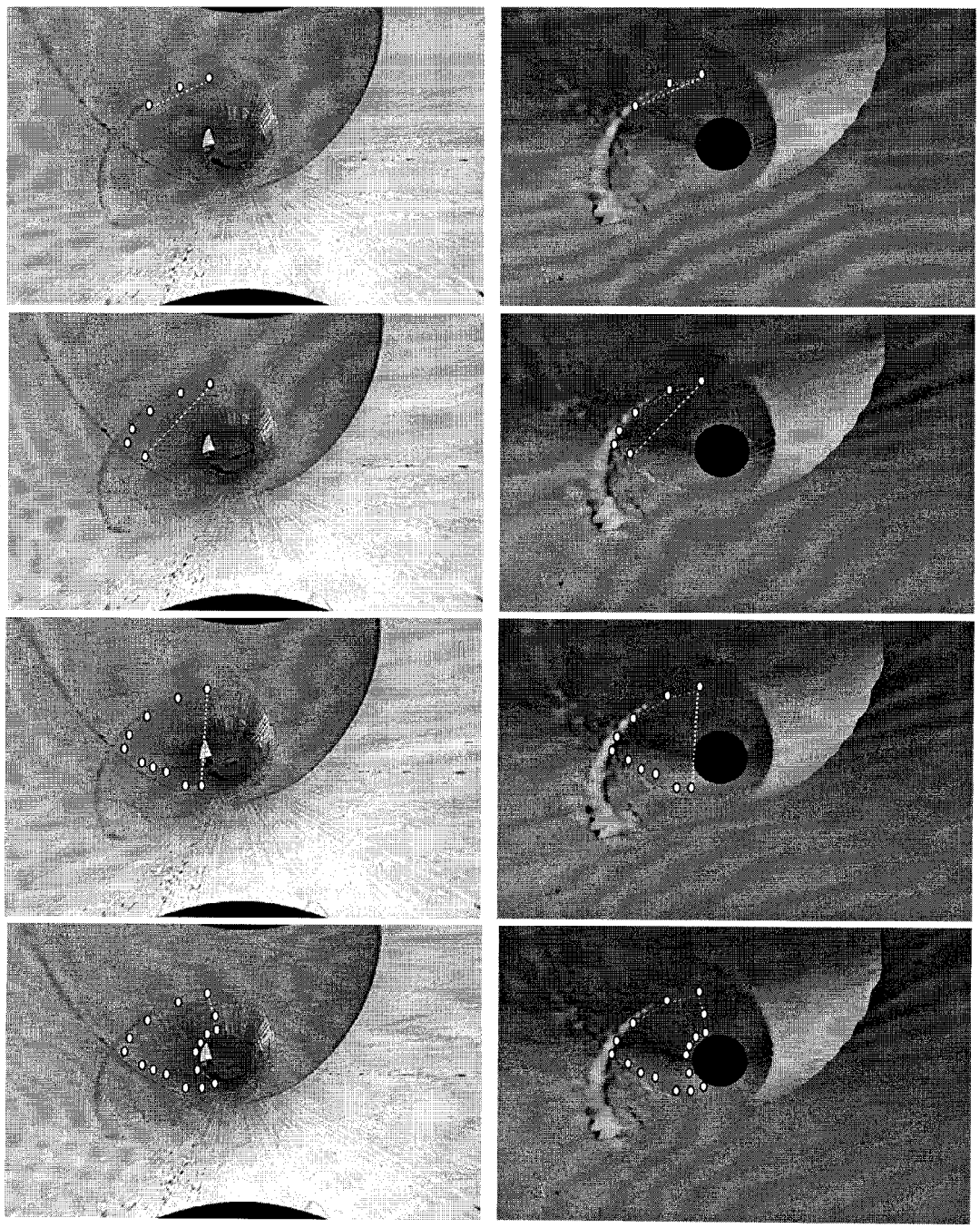
FIG. 4 shows an example display of example software suitable to carry out the method of FIG. 1.

FIG. 4 shows an example of a screen display provided by example software during the contouring process, in this example using a phantom. The display shows points picked in the endoscopic image registered and placed in the CT view. A complete contour may then be traced out, outlining the region of interest. While the points picked in the endoscopy image are only in 2D, due to the registration with the CT images, and due to the rendering tools, the required 3D coordinate may be identified. Hence the 2D ROI has been projected from 2D into 3D.

In some examples, the region of interest outlined by the contour may be further filled in. This may be completed using standard techniques. An example would be to fill in the contour shape in the 2D image with a series of triangles, to generate a 2D mesh. The points of these triangles may also be projected into the 3D space. The result may be a filled in volume or surface that can be, for example, exported and read by other treatment planning software.

The 3D surface may be stored and/or transmitted for further use. For example, the 3D mesh may be exported in a format that may be imported into standard clinical treatment planning software (e.g., for radiotherapy). Multiple regions may be thus contoured and exported for planning.

In some examples, the example method may be performed with a single software component (e.g., developed using Visual Toolkit (VTK) and Image Guided Surgery Toolkit (IGSTK) toolkits). In some examples, the example method may be performed with multiple software components residing in one or more processors. Conventional algorithms for image data processing and visualization, tool tracking and registration may be used.

Figure 5A:
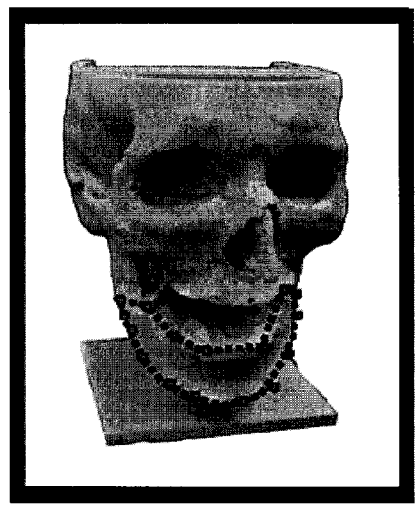
FIGS. 5A and 5B illustrate an example of a ROI processed according to the method of FIG. 1.
Figure 5A:
Figure 5A:
Figure 5A:
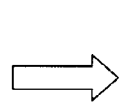
Figure 5A:
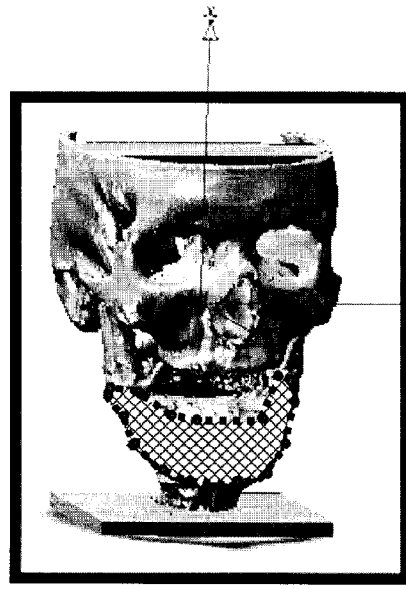
Figure 5B:
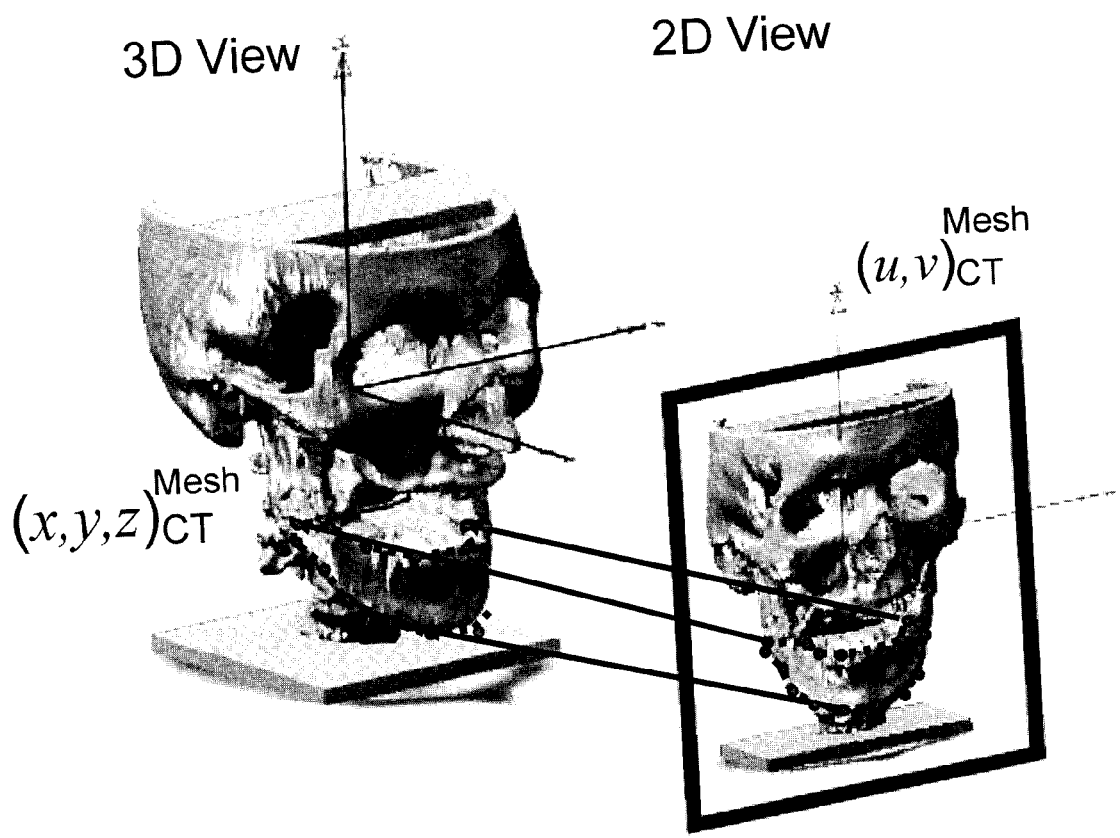

FIGS. 5A and 5B illustrate an example of the example method described above, applied to a model of a human skull. In the top of FIG. 5A, a region of interest is identified in the original 2D image, creating a 2D contour. These points, identified as $(u,v)_S$, are overlaid on the virtual 2D view rendered from the 3D image (bottom left, FIG. 5A), based on the camera position of the real image as determined by the tracking of the endoscope, giving a set of points, identified as $(u,v)_{CT}$, which is a 2D view in the common coordinate system. This may be performed using the registration of the endoscopic dataset with the volumetric dataset. The region of interest also typically contains topographic features within the contour defined by $(u,v)_{CT}$ that also need to be identified on the 3D surface. To identify the whole of the surface within $(u,v)_{CT}$, the interior of the region of interest is filled with, for example, a mesh consisting of connected triangles. In the example shown, (bottom right, FIG. 5A) this mesh is defined by $(u,v)_{CT}^{Mesh}$. The set of points and filled-in region (e.g., the mesh) in the virtual image $(u,v)_{CT}$ (right, FIG. 5B) are then projected onto the 3D surface, for example with a thresholding technique used to identify when the projection has hit the surface. This projection gives the final set of 3D points (left, FIG. 5B), identified as $(x,y,z)_{CT}$, that may be exported into a file, for example, that can be read by treatment planning software for radiotherapy.

EXAMPLE

An example of the disclosed method is now described, with reference to an example study.

In this example, electromagnetic (EM) tracking and/or optical tracking may be used to track the position of the endoscope, depending on the type of endoscope used. Typically, the smaller sensors used with EM tracking may be suitable for flexible endoscopes, such as laryngeal endoscopes used in head and neck diagnosis & staging. The EM tracking system (e.g., the Aurora system from Northern Digital, Waterloo, Ontario, Canada) used in this example may have sensors that track either 5 (x, y, z, Φ, φ)), or 6 (x, y, z, φ, φ, θ) degrees of freedom (DoF) located at the distal end of the endoscope. Where 6 DoF are sensed by the sensor, a single sensor may be used. Where only 5 DoF are sensed by the sensor, two such sensors may be used to cover all six DoF.

In this example, The 5 DoF and 6 DoF tracking sensors are 0.5 and 1.8 mm in diameter, respectively. All 6 degrees of freedom may be used to track the orientation of the endoscopic image within the volumetric (in this example, CT) image set. In this example study, a single 6 DoF sensor was placed within the working channel of a flexible bronchoscope (e.g., Evis Extera II Gastrointestinal Videoscope, Olympus, Canada). This endoscope may provide high definition video images using a charge-coupled device (CCD) placed at the distal end of the endoscope.

In another example, two 5 DoF tracking sensors may be placed on opposite sides on the outside of the endoscope. The orientation of the plane intercepting these two sensors may be used to define the orientation of the scope about the axis along the length of the endoscope. This may be useful, for example, where the 6 DoF tracking sensor is too large to place in the working channel of the endoscope, such as in the flexible laryngoscopes typically used in diagnosing and staging head and neck patients.

In some examples, such as for rigid endoscopes, a conventional optical tool may be attached to the proximal end of the endoscope (e.g., Polaris, Northern Digital, Waterloo, Ontario, Canada). While the rigid endoscope may have limited range within the patient, optical tools may be more accurate and may not suffer from artifacts due to the presence of ferromagnetic materials.

In some examples, calibration of the endoscopic camera's intrinsic properties is required to determine the camera focus and to correct the significant radial or "fisheye" distortion apparent in the native images. Typically, extrinsic camera calibration is also required to register the camera position with respect to the tracking sensor(s) and hence to the world coordinate space (i.e., endoscopic navigation space).

In this example, both of these calibration procedures were performed simultaneously by imaging from several orientations a black and white 10×10 checkerboard with each block 5 mm in length. Calibration was performed using the Camera Calibration Toolbox (http://www.vision.caltech.edu/bouguetj/calib_doc/) developed for MatLab (Mathworks, Natick, Mass.), modified to export camera coordinates. Corners were automatically identified in each image and used as test points for the model development. Radial distortion and skewing was modeled as camera radial calibration.

Rigid registration between the endoscopic camera and the tracking sensor (in this example, a single EM sensor) was then determined from the camera positions derived from the calibration process and the corresponding coordinates of the tracking sensor for each image. The distortion-corrected endoscopic image was mapped in real-time to a plane in the software, for example using the Visualization Toolkit (VTK), which is placed in a 3D scene (e.g., within the 3D volumetric imaging dataset), allowing overlay of geometrically corrected endoscopic images with the 3D rendering.

Figure 2:
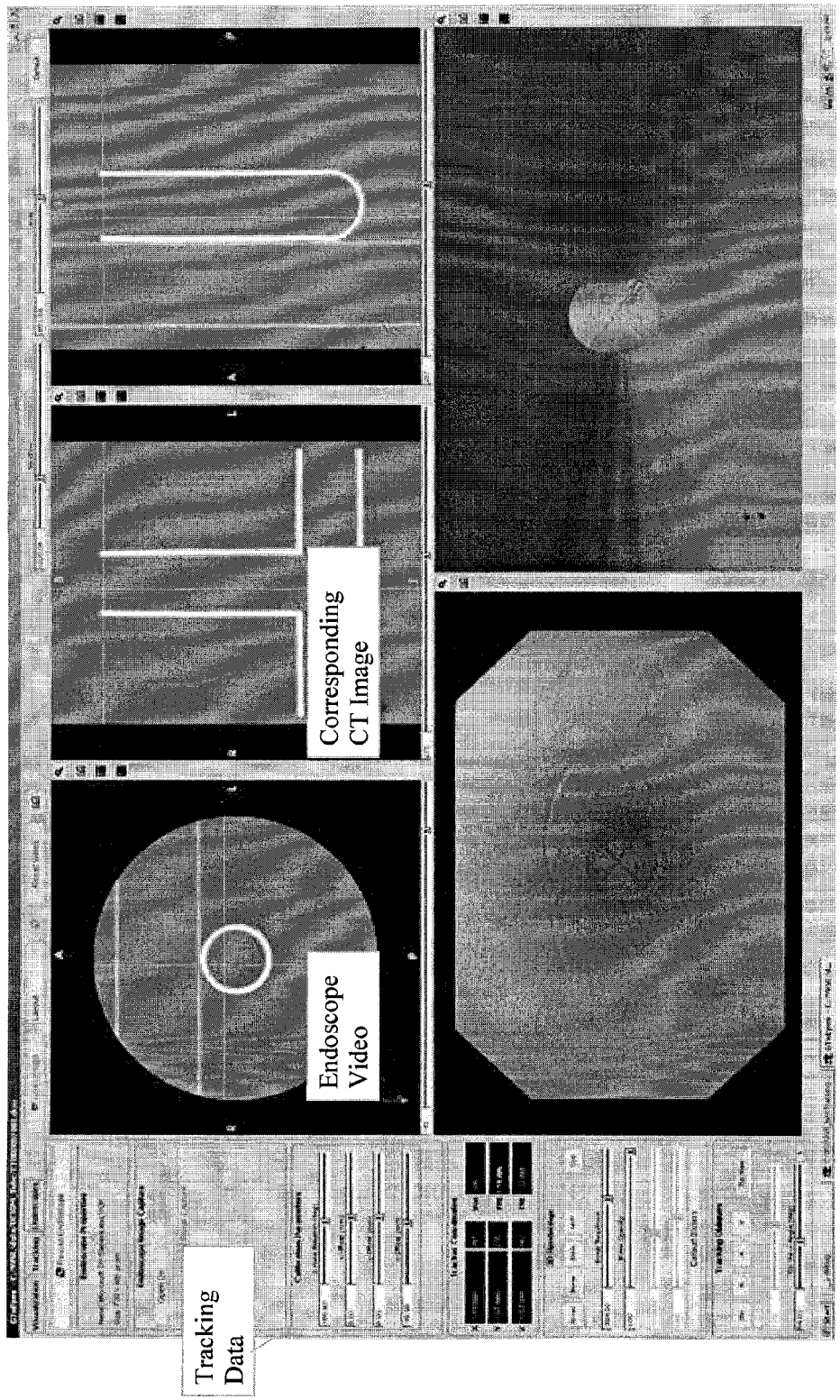
FIG. 2 shows an example display of example software suitable to carry out the method of FIG. 1.

An example screen shot of example software is shown in FIG. 2. In this example, the screen displays endoscopic and rendered CT views of a phantom, using tracking coordinates (e.g., electromagnetic tracking coordinates). Tracking information is provided on the left. The top row shows the standard 3 views (coronal, axial, sagittal) of a CT image of a plastic phantom. In this example, the position of the crosshairs in each image indicates the position of the endoscope tip, while the orientation is indicated by a green line (barely visible in this image). Other methods of displaying this information may also be suitable. The lower row shows on the left the endoscopic view at this position. The bottom right figure is a rendering of the structure based on the CT data, from the position and orientation provided by the tracking.

In this example, contouring was performed retrospectively using the same software as data collection. However, it should be understood that in other examples, the contouring process and the registration process may be carried out by separate software components and may be carried out by separate processors (e.g., separate workstations or computers). In this example, the volumetric imaging data (in this case, CT image data) and the endoscopic data were stored in the same database, however they may be stored in separate databases and related to each other, for example, through the use of indices or other conventional methods.

In this example, the volumetric (e.g., CT) image is loaded followed by an endoscope image and its respective tracking coordinates and camera calibration information. The example software displays the endoscope image in one window and a virtual endoscope view based on a rendering of the volumetric image from the camera position defined by the tracking coordinates. The virtual endoscope view represents a projection of the 3D volumetric surface onto an image plane that is centered on the camera and perpendicular to its optical axis. The coordinate systems used and a general schematic of the contouring process may be as described above, for example as shown in FIGS. 3 and 5. The coordinates of any pixel within the real and virtual endoscope views may be referred to as $(u,v)_S$ and $(u,v)_{CT}$ respectively.

In the example software, the region of interest in the real endoscope view is outlined by clicking several points on the perimeter of the region, defining the region of interest, $(u,v)_S$. Using the mapping model between the real and virtual views, the perimeter of the region of interest (ROI) can be defined in the virtual CT view, defined as $(u,v)_{CT}$. The ROI can contain both convex and concave curves. In this example, Delaunay triangulation (CGAL, Computational Geometry Algorithms Library, http://www.cgal.org) is used to generate a triangular 2D mesh within the traced ROI using, a set of points defined as $(u,v)_{CT}^{Mesh}$. Other algorithms for generating a mesh may also be used. In order to preserve concavity, in this example a recursive traversal of outer triangles was used to label and remove triangles outside of $(u,v)_{CT}$. Neighbouring triangles that do not share a boundary edge of the ROI may be labeled as outside and removed. The 2D mesh points may be transposed through the camera model, and projected onto the 3D rendered surface, giving the coordinates of the points in the 3D image coordinate space $(x, y, z)^{Mesh}$. The triangle relationships that define the 2D mesh may be maintained during the transpose and projection steps, and so the 3D mesh may now be defined in 3D coordinates. Other methods of generating a mesh may also be used.

The 3D mesh may also be stored in the database for future use, or may be transmitted for further analysis. For example, the 3D mesh given by $(x, y, z)^{Mesh}$ may transmitted for radiotherapy treatment planning. For example, the 3D mesh may be exported into a format that can be read by Pinnacle Treatment planning software. This may be done a variety of ways. For example, the 3D mesh may be exported as is into either a standard VTK mesh file, or into a Pinnacle ROI file format. In another example, contour lines may be derived in each slice of the original volumetric image by interpolation through the 3D mesh. These contour lines may be exported as either DICOM™ format or again as Pinnacle ROI files.

An example of the disclosed method was verified in an example study. The example method described above was tested using an anatomically correct plastic phantom of a human skull that was generated by rapid prototyping off of a patient image. Navigation points were also added to the interior surface of the phantom. Approximately ¼ of these were 2 mm in diameter and 1 mm tall, with a 1 mm diameter pit in the center. These were used for assessing registration accuracy of various tracking tools. The remainders were 0.8 mm in diameter and 0.5 mm tall and were used as identification markers for assessing registration accuracy. These were spaced 1-3 cm apart on the phantom surface and are visible in the CT and endoscope images.

Using standard patient protocol for a head and neck case, a CT simulation image was taken of the phantom. This image set was used as the baseline for both navigation and endoscopy and for planning in the treatment planning software. For the endoscopy procedure, the phantom was placed within the EM tracking field of view, the CT image loaded into the navigation/registration software, and the image registered to the coordinate space of the phantom using 15 fiducial markers on the outside of the phantom. The endoscopy procedure was performed on the phantom, capturing images from several distinct locations within the phantom.

Contouring was performed retrospectively using the example method and software described above. 3D surface meshes created for each ROI were exported into a format that could be read by the treatment planning software (Pinnacle V.

8). The correspondence of the mesh with the surface of the phantom was inspected visually.

Figure 6A:
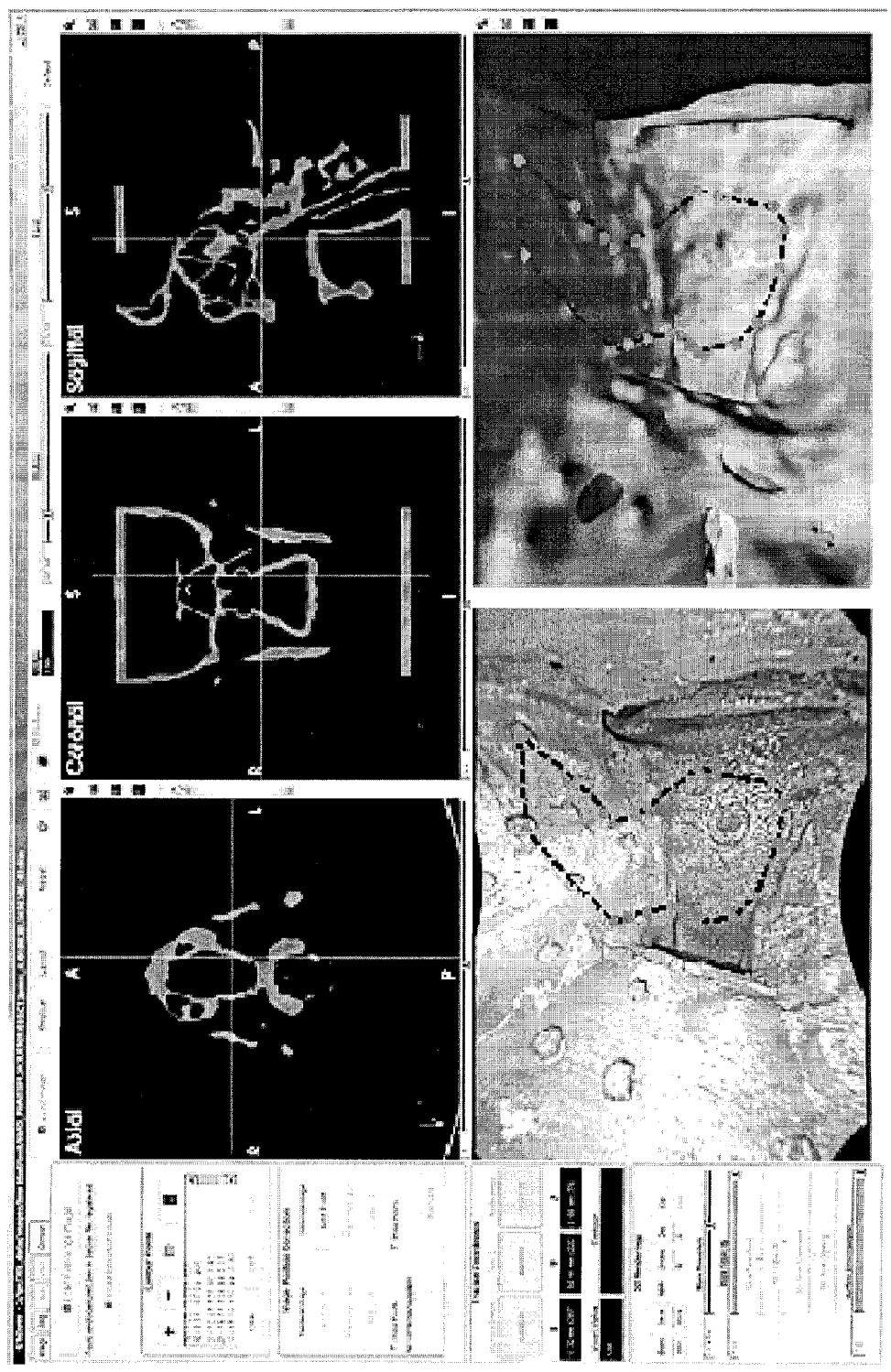
FIGS. 6A and 6B show example displays of example software suitable to carry out the method of FIG. 1.
Figure 6B:
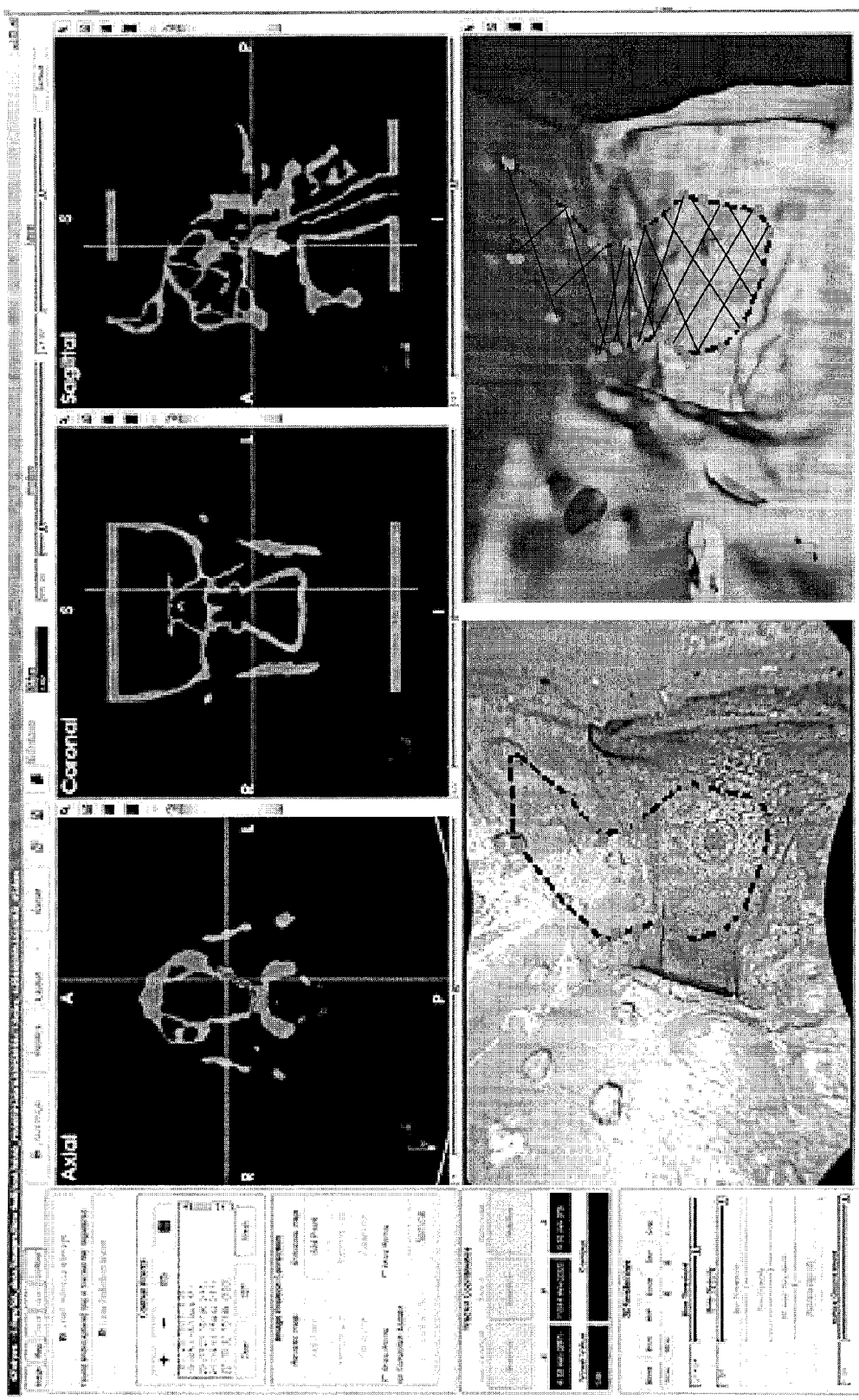

Examples of the resultant contouring are shown in FIGS. 6A and 6B, which show screen shots of an example contouring software. In each of FIGS. 6A and 6B, the 2D endoscopic view is shown in the bottom left of the screen shot, with an ROI traced out. This ROI has been transferred to the virtual view (bottom right in each of FIGS. 6A and 6B) based on the camera position indicated by the tracking data of the endoscopic dataset. Note the concordance of the ROI position with the small markers present on the real and virtual images. In FIG. 6B, the interior of the ROI has been filled in with a tight mesh of points (indicated as a cross-hatch pattern). These points have been projected onto the surface, in this example using a threshold technique in which the projection perpendicular to the screen continues in free space through the volumetric space until it passes through a voxel that has a CT number higher than a user set threshold value. This voxel identifies the 3D location of this point. Other suitable projection methods may be used.

Figure 7:
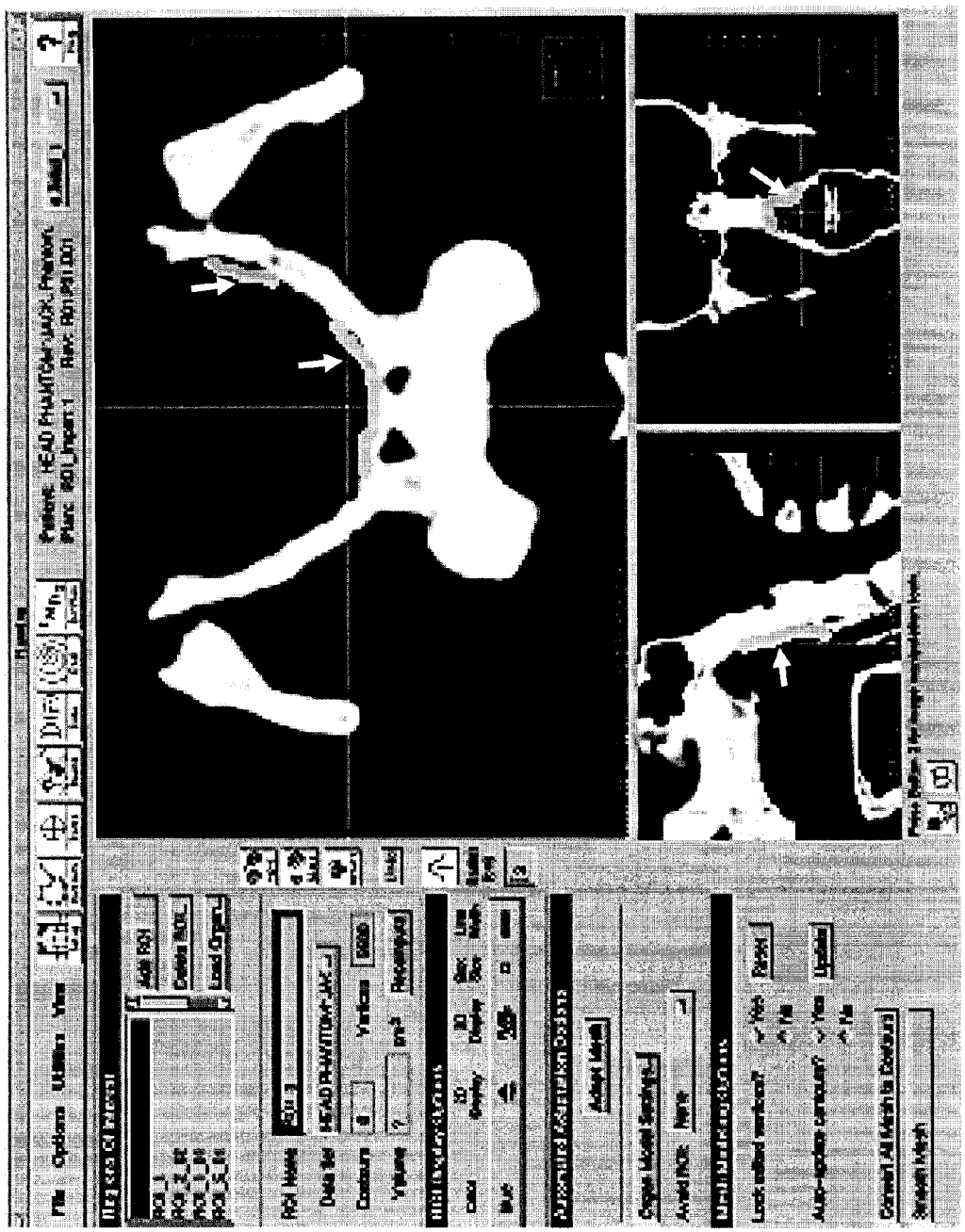
FIG. 7 shows an example display of a registered 3D ROI generated according to the method of FIG. 1.

The 3D mesh may be imported into the treatment planning software. FIG. 7 shows an example screen shots of an example treatment planning software. The contour shown (indicated by arrows in 3 different views) is from the ROI identified in FIGS. 6A and 6B. The contour matches the surface of the phantom, indicating registration of the 2D ROI with the 3D treatment planning structure.

The example method was found to relatively accurately and quantitatively register 2D ROI information with 3D volumetric imaging data, which may be used in radiation treatment planning and delivery. This may be done with an accuracy of ±1 mm, in the present example. Further improvements in registration accuracy may be gained by conventional image registration techniques, such as using feature extraction or mutual information algorithms between the real and virtual endoscope images. The disclosed method may also be adapted to integrate other forms of 2D imaging information such as fluorescence endoscopy (which may be able to delineate tumor extent better than standard white light endoscopy, and thus the clinical target volume) and endoscopic ultrasound.

APPLICATIONS

Although the above example describes the use of CT imaging as the volumetric imaging dataset, other suitable volumetric imaging datasets may also be used, including, for example, magnetic resonance (MR) imaging datasets and positron emission tomography (PET) imaging dataset. Suitable endoscopic imaging datasets may include, for example, fluorescence endoscopic imaging datasets (which may be either native (endogenous) or contrast-enhanced (exogenous)), optical coherence tomography (OCT) endoscopic imaging datasets, ultrasound (US) endoscopic imaging datasets, and point fluorescence endoscopic measurements.

Although the disclosed methods and techniques have been described for use in treatment planning and delivery for radiotherapy, these methods and techniques may also be useful in other areas in which information gathering or delineation of a treatment target is done using 2D images while treatment planning or delivery is done in 3D.

The embodiments of the present disclosure described above are intended to be examples only. Those of skill in the art may effect alterations, modifications and variations to the particular embodiments without departing from the intended scope of the present disclosure. In particular, selected features from one or more of the above-described embodiments may be combined to create alternative embodiments not explicitly described, features suitable for such combinations being readily apparent to persons skilled in the art. The subject matter described herein in the recited claims intends to cover and embrace all suitable changes in technology. All references mentioned are hereby incorporated by reference in their entirety.

REFERENCES

1. Rosenthal, D. I., Asper, J. A., Barker, J. L. et al.: Importance of patient examination to clinical quality assurance in head and neck radiation oncology. Head and Neck-Journal for the Sciences and Specialties of the Head and Neck, 28: 967, 2006
2. Sharma, P., Bansal, A., Mathur, S. et al.: The utility of a novel narrow band imaging endoscopy system in patients with Barrett's esophagus. Gastrointestinal Endoscopy, 64: 167, 2006
3. Wilson, B. C.: Detection and treatment of dysplasia in Barrett's esophagus: a pivotal challenge in translating biophotonics from bench to bedside. Journal of Biomedical Optics, 12, 2007
4. Kara, M. A., Peters, F. P., Fockens, P. et al.: Endoscopic video-autofluorescence imaging followed by narrow band imaging for detecting early neoplasia in Barrett's esophagus. Gastrointestinal Endoscopy, 64: 176, 2006
5. Fried, M. P., Parikh, S. R., Sadoughi, B.: Image-Guidance for Endoscopic Sinus Surgery. Laryngoscope, 118: 1287, 2008
6. Caversaccio, M., Giraldez, J. G., Thoranaghatte, R. et al.: Augmented reality endoscopic system (ARES): preliminary results. Rhinology, 46: 156, 2008
7. Higgins, W. E., Helferty, J. P., Lu, K. K. et al.: 3D CT-Video Fusion for Image-Guided Bronchoscopy. Computerized Medical Imaging and Graphics, 32: 159, 2008
8. Lapeer, R., Chen, M. S., Gonzalez, G. et al.: Image-enhanced surgical navigation for endoscopic sinus surgery: evaluating calibration, registration and tracking. International Journal of Medical Robotics and Computer Assisted Surgery, 4: 32, 2008
9. Lindbergh, T., Larsson, M., Fredriksson, I. et al.: Reduced scattering coefficient determination by non-contact oblique angle illumination: methodological considerations—art. no. 64350I. Optical Interactions with Tissue and Cells XVIII, 6435: I4350, 2007
10. Lin, S. P., Wang, L. H., Jacques, S. L. et al.: Measurement of tissue optical properties by the use of oblique-incidence optical fiber reflectometry. Applied Optics, 36: 136, 1997
11. Gebhart, S. C., Mahadevan-Jansen, A., Lin, W. C.: Experimental and simulated angular profiles of fluorescence and diffuse reflectance emission from turbid media. Applied Optics, 44: 4884, 2005
12. Qu, J. Y., Hua, J. W., Huang, Z. J.: Correction of geometrical effects on fluorescence imaging of tissue. Optics Communications, 176: 319, 2000
13. Qu, J. N. Y., Huang, Z. J., Hua, J. W.: Excitation-and-collection geometry insensitive fluorescence imaging of tissue-simulating turbid media. Applied Optics, 39: 3344, 2000
14. Wang, H., Mirota, D., Hager, G. et al.: Anatomical reconstruction from endoscopic images: Toward quantitative endoscopy. American Journal of Rhinology, 22: 47, 2008

The invention claimed is:

1. A method for quantitatively registering a 2D endoscopic region of interest (ROI) in a 3D volumetric imaging dataset, the method comprising:

receiving signals representing the volumetric imaging dataset;

receiving signals representing an endoscopic dataset from an endoscope, the endoscopic dataset including an endoscopic imaging dataset and a tracking dataset, the tracking dataset including information about the position and orientation of the endoscope;

wherein coordinates of the endoscopic dataset and coordinates of the volumetric imaging dataset are registered to a common coordinate system;

receiving a definition of the 2D endoscopic ROI within the endoscopic imaging dataset, the 2D endoscopic ROI being outlined on a 2D endoscopic image by a 2D contour generated based on clinical examination;

generating a 3D surface ROI within the volumetric imaging dataset corresponding to the 2D endoscopic ROI, based on a projection of the 2D endoscopic ROI to the registered common coordinate system; and transmitting signals representing the generated 3D surface ROI for treatment planning.

2. The method of claim 1 further comprising:

generating the 2D contour of the 2D endoscopic ROI by defining points within the contour.

3. The method of claim 1 further comprising:

registering the volumetric imaging dataset to the common coordinate system using reference markers.

4. The method of claim 3 wherein the reference markers are fiducial markers or anatomical features.

5. The method of claim 1 further comprising:

registering the volumetric imaging dataset to the common coordinate system using a 3D model based on the endoscopic imaging dataset.

6. The method of claim 1 further comprising:

displaying the 3D surface ROI superimposed on a 3D image generated from the volumetric imaging dataset.

7. The method of claim 1 wherein the common coordinate system is one of: a real world coordinate system, an endoscopic coordinate system of the endoscopic dataset, and a volumetric coordinate system of the volumetric imaging dataset.

8. The method of claim 1 wherein the volumetric imaging dataset is one of: a computer tomography (CT) imaging dataset, a magnetic resonance (MR) imaging dataset, and a positron emission tomography (PET) imaging dataset.

9. The method of claim 1 wherein the endoscopic dataset is one of: a fluorescence endoscopic dataset, an endoscopic ultrasound dataset, a surgical endoscopic dataset, a white light endoscopic dataset, and a narrow-band endoscopic dataset.

10. A non-transitory computer readable medium comprising computer executable instructions embodied therein that when executed by at least one processor, cause the at least one processor to carry out the method of claim 1.

11. A computer system comprising at least one processor coupled to a non-transitory computer readable medium, the non-transitory computer readable medium comprising computer executable instructions embodied therein that when executed by the at least one processor cause the at least one processor to carry out the method of claim 1.

* * * * *